United States Patent
Fan et al.

(10) Patent No.: US 11,338,263 B2
(45) Date of Patent: May 24, 2022

(54) CONTINUOUS SLURRY-BED TANK REACTOR AND METHOD OF USING SAME

(71) Applicants: Institute of Coal Chemistry, Chinese Academy of Sciences, Taiyuan (CN); Shanxi Lu'an Mining (Group) Co., Ltd., Changzhi (CN)

(72) Inventors: Weibin Fan, Taiyuan (CN); Guofu Wang, Taiyuan (CN); Jiaqi Guo, Taiyuan (CN); Jianguo Wang, Taiyuan (CN); Mei Dong, Taiyuan (CN); Youliang Cen, Taiyuan (CN); Yaning Xiao, Taiyuan (CN); Dongfei Wang, Taiyuan (CN); Shoujing Sun, Taiyuan (CN); Weilin Wang, Taiyuan (CN); Juncai Zhang, Taiyuan (CN); Min Zhang, Taiyuan (CN); Yunhong Li, Taiyuan (CN)

(73) Assignees: Institute of Coal Chemistry, Chinese Academy of Sciences, Taiyuan (CN); Shanxi Lu'an Mining (Group) Co., Ltd., Changzhi (CN)

(*) Notice: Subject to any disclaimer, the term of this patent is extended or adjusted under 35 U.S.C. 154(b) by 0 days.

(21) Appl. No.: 16/849,396

(22) Filed: Apr. 15, 2020

(65) Prior Publication Data
US 2020/0338516 A1  Oct. 29, 2020

(30) Foreign Application Priority Data
Apr. 29, 2019  (CN) .......................... 201910356734.6

(51) Int. Cl.
| | |
|---|---|
| *B01J 8/10* | (2006.01) |
| *B01F 7/22* | (2006.01) |
| *B01D 65/02* | (2006.01) |
| *B01J 8/08* | (2006.01) |
| *B01J 8/00* | (2006.01) |
| *C07C 249/08* | (2006.01) |
| *C07C 41/03* | (2006.01) |
| *B01F 27/91* | (2022.01) |
| *B01F 101/00* | (2022.01) |

(52) U.S. Cl.
CPC ................ *B01J 8/10* (2013.01); *B01D 65/02* (2013.01); *B01F 27/91* (2022.01); *B01J 8/0065* (2013.01); *B01J 8/082* (2013.01); *B01J 8/085* (2013.01); *C07C 41/03* (2013.01); *C07C 249/08* (2013.01); *B01D 2321/2083* (2013.01); *B01F 2101/2204* (2022.01); *B01J 2208/00061* (2013.01); *B01J 2208/0061* (2013.01); *B01J 2208/00539* (2013.01); *B01J 2208/00548* (2013.01); *B01J 2208/00867* (2013.01); *B01J 2208/00902* (2013.01)

(58) Field of Classification Search
CPC . B01J 8/10; B01J 8/0065; B01D 65/02; B01F 7/22
See application file for complete search history.

(56) References Cited

U.S. PATENT DOCUMENTS 7,569,196 B2 * 8/2009 Zanthoff ............. B01F 7/00641
                                                     210/225

FOREIGN PATENT DOCUMENTS

| CN | 106220481 | * 12/2016 | ............. C07C 41/56 |
|---|---|---|---|
| CN | 106220481 B | 11/2018 | |
| EP | 2177260 A1 | * 4/2010 | ............. B01J 19/18 |

* cited by examiner

*Primary Examiner* — Yong L Chu
(74) *Attorney, Agent, or Firm* — Osha Bergman Watanabe & Burton LLP

(57) ABSTRACT

A continuous slurry-bed tank reactor, comprising a tank reactor body, an agitator, and tubular separation membranes. A method of using the continuous slurry-bed tank reactor comprising adding a catalyst, feeding reactants, stopping feeding the reactants, starting a heating system, changing directions of the reactants flowing through the tubular separation membranes.

6 Claims, 2 Drawing Sheets

CONTINUOUS SLURRY-BED TANK REACTOR AND METHOD OF USING SAME

TECHNICAL FIELD

The present invention relates to the technical field of tank reactors, and specifically to a slurry-bed tank reactor and a method of using the tank reactor, wherein materials are continuously fed into and discharged from the tank reactor.

BACKGROUND

A tank reactor is widely applied in industry. On the basis of operation mode, the tank reactor may be classified as a batch tank reactor, a semibatch tank reactor and a continuous tank reactor. In the continuous tank reactor, materials are continuously fed and discharged to achieve continuous operations and high efficiency. However, it is still a challenge to continuously operate a heterogeneous reaction in a tank reactor. Chinese Patent Application No. 2016105989527 provides a continuous operation method, but in the running process, solid powders are often adhered to tubular separation membranes, and hence, affecting the continuity of running, and the reflection of long catalytic life of a catalyst.

SUMMARY

To solve technical problems occurred in continuously operating a heterogeneous reaction in a tank reactor and to fully make use of the long catalytic life of a catalyst, one or more embodiments of the present invention provides a continuous slurry-bed tank reactor and a method of using it. One or more embodiments of the present invention provides a slurry-bed tank reactor in which a nanomaterial-based catalyst and reactants are directly separated. One or more embodiments of the present invention is applicable to catalysts with small particle sizes, even raw molecular sieve powder catalysts. Liquid materials and a catalyst are uniform slurries in the reactor, and reactants are fed into and discharged from the reactor in an uninterrupted and continuous operation manner.

One or more embodiments of the present invention is achieved by the following.

A continuous slurry-bed tank reactor comprises a tank reactor body, an agitator and tubular separation membranes.

The tank reactor body is equipped with a thermocouple for measuring the temperature of reaction mixture inside the tank reactor body, a liquid level gauge for measuring the liquid level inside the tank reactor body, a third pressure gauge for measuring the pressure inside the tank reactor body, and a gas flow controller for measuring the gas flow rate into the tank reactor body.

The agitator comprises an agitation motor, an agitation shaft and an agitation impeller. The agitation motor is located at the center over the tank reactor body. The rotor of the agitation motor is vertically downwards set up. One end of the agitation shaft is fixedly connected with the rotor of the agitation motor, and the other end thereof penetrates through the upper cap of the tank reactor body and extends to the bottom of the tank reactor body. The agitation impeller is installed at the bottom of the agitation shaft.

The tubular separation membranes comprise A and B tubular separation membranes, which are respectively vertically downwards set up on the two sides of the agitation shaft. The first and the second openings of the continuous slurry-bed tank reactor are respectively communicated with two transversely symmetrical ports of a four-way valve. The A and the B tubular separation membranes are respectively communicated with two longitudinally symmetrical ports of the four-way valve. The liquid was not simultaneously fed or discharged from the first and the second openings. A liquid feed pump is set up at the first opening and connected with the first counterbalance valve in parallel. The first pressure gauge is installed at the first counterbalance valve. The second counterbalance valve is positioned at the second opening, and in a pipeline connecting second counterbalance valve and the upper port of the four-way valve, a second pressure gauge is installed.

In addition, at least two auxiliary material spargers are installed at the lower portion of the side wall of the tank reactor body, and each one extends into the tank reactor body, is set up at a different position in the tank reactor body, and is communicated with an auxiliary material feed pump through another pipeline.

A method of using the continuous slurry-bed tank reactor comprises the following steps:

S1: adding a catalyst into the tank reactor body, and filling nitrogen gas in the tank reactor body by a gas flow controller until all air in the tank reactor body is replaced with nitrogen gas, wherein the gas flow controller measures and controls the flow rate of the nitrogen gas filled in the tank reactor body;

S2: feeding reactants into the tank reactor body sequentially through the liquid feed pump, the four-way valve and the A tubular separation membrane; using a liquid level gauge to measure the liquid level of the fed reactants and ensure that a distance between the liquid level of the reactants and the top cap of the tank reactor body is in the range of 5-80 cm; presetting the opening pressure of the first counterbalance valve to a value lower than the designed pressure of the tank reactor body by 0.3-0.5 MPa;

S3: when the liquid level of the reactants reaches the preset lower limit, stopping feeding the reactants; opening a heating system in the tank reactor body to raise the internal temperature of the tank reactor body to the preset temperature; opening the agitation system; determining the internal pressure of the tank reactor body at this moment as the initial pressure, and setting the opening pressure of the second counterbalance valve to be 0.3-0.8 MPa higher than the initial pressure; maintaining the temperature for 1-3 hours after the internal temperature of the tank reactor body is elevated to the preset temperature; turning on the liquid feed pump again to start continuously feeding the reactants;

S4: setting the four-way valve to switch flow paths once every 4-8 hours for altering the directions of reaction mixture flowing through the tubular separation membranes; resetting the four-way valve to switch the flow paths and recalculating the flow path switching time when the internal pressure of the tank reactor body is higher than the initial pressure by 0.8-1.0 MPa; stopping feeding the reactants when the time interval for switching the flow path is shorter than 2 hours because of the increase in the internal pressure of the tank reactor body.

Further, in step S2, at least two auxiliary material spargers are installed at the lower portion of the side wall of the tank reactor body. The auxiliary material feed pump adds reactants with poor miscibility in the tank reactor body through the auxiliary material spargers.

Further, in step S3, when the liquid feed pump starts to continuously feed the reactants, the gas flow controller is turned on. At the beginning, a small flow of nitrogen gas is filled. Afterwards, the flow rate of nitrogen gas is dynamically adjusted in terms of the changes of the liquid level.

When the liquid level of the reaction mixture is close to the liquid level upper limit, the flow rate of nitrogen gas is increased. On the contrary, while the liquid level of the reaction mixture is approaching to the liquid level lower limit, the flow rate of nitrogen gas is reduced. When the liquid level of the reaction mixture exceeds the liquid level upper limit, the four-way valve is triggered to switch the flow paths. If the flow path switching time interval of the four-way valve is shorter than 2 hours due to the increase of the internal pressure of the tank reactor body, the filling of nitrogen gas would be stopped by closing the gas flow controller.

Further, the feeding amount of the liquid feed pump is determined to be 0.3-50 $h^{-1}$ of the weight hourly space velocity on the basis of the reactant conversion and the product selectivity.

When the flow path switching time interval of the four-way valve is decreased due to the increase of the internal pressure or the change of the liquid level, the feeding amount of the reaction mixture is reduced until the catalytic performance of the catalyst or the permeability of the tubular separation membranes cannot meet the demands.

One or more embodiments of the present invention have the following beneficial effects:

1, a slurry-bed reactor can allow a molecular sieve catalyst with small particle size fully show its excellent catalytic performance as a result of significantly weakening, and even eliminating the internal diffusion effect, thereby realizing high conversion of raw materials and high selectivity to products;

2, a conventional solid-liquid separation process is omitted by utilizing tubular separation membranes that the reactants and the catalyst are directly separated in the tank reactor so as to improve the working efficiency;

3, in a dual-mode time division countercurrent flow mode, adhesion of the solid catalyst to the tubular separation membranes is surmounted, the time of continuous and stable operation is prolonged, and the long catalytic life of the catalyst can be effectively reflected.

Figure 1:
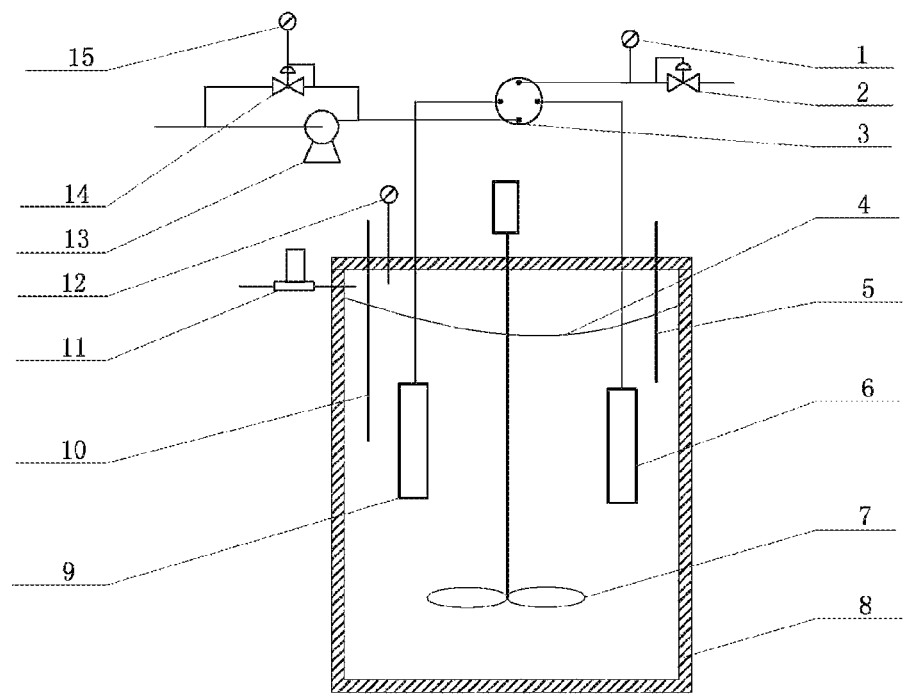
FIG. 1 is a schematic structural diagram of a continuous slurry-bed tank reactor.

In the drawings: 1—second pressure gauge, 2—second counterbalance valve, 3—four—way valve, 4—liquid level, 5—liquid level gauge, 6—B tubular separation membrane, 7—agitation system, 8—tank reactor body, 9—A tubular separation membrane, 10—thermocouple, 11—gas flow controller, 12—third pressure gauge, 13—liquid feed pump, 14—first counterbalance valve, 15—first pressure gauge, 16—auxiliary material feed pump, and 17—auxiliary material sparger.

DETAILED DESCRIPTION OF THE EMBODIMENTS

The following further describes one or more embodiments of the present invention in detail with reference to the accompanying drawings and embodiments.

As shown in FIG. 1, a continuous slurry-bed tank reactor comprises a tank reactor body 8, an agitator 7 and tubular separation membranes.

The tank reactor body 8 is equipped with a thermometer (10) for measuring the reaction mixture temperature inside the tank reactor body (8), a liquid level gauge (5) for measuring the liquid level inside the tank reactor body (8), a third pressure gauge (12) for measuring the internal pressure of the tank reactor body 8, and a gas flow controller 11 for measuring and controlling the gas flow rate into the tank reactor body (8).

The agitator 7 comprises an agitation motor, an agitation shaft and an agitation impeller. The agitation motor is set up at the center over the tank reactor body (8). A rotor of the agitation motor is vertically downwards installed. One end of the agitation shaft is fixedly connected with the rotor of the agitation motor, and the other end thereof penetrates through the upper cap of the tank reactor body (8) and extends to the bottom of the tank reactor body (8). The agitation impeller is installed at the bottom of the agitation shaft.

The tubular separation membranes comprise an A tubular separation membrane (9) and a B tubular separation membrane (6), which are respectively vertically downwards located on the two sides of the agitation shaft. The B tubular separation membrane (6) and the A tubular separation membrane (9) are installed in the continuous tank reactor to achieve solid-liquid separation. The tubular separation membranes utilize stainless steel tubes fabricated in a powder metallurgy manner as the substrates, and their permeability is finely adjusted through chemical vapor deposition, thereby meeting double demands of good permeability and effective separation of solid catalysts with different particle sizes and liquid reactants. The first and the second openings of the continuous slurry-bed tank reactor are respectively communicated with two transversely symmetrical ports of the four-way valve (3). The A tubular separation membrane (9) and the Bd tubular separation membrane (6) are respectively communicated with two longitudinally symmetrical ports of the four-way valve (3). The first opening and the second opening do not simultaneously feed or discharge liquid. A liquid feed pump (13) is positioned at the first opening and connected with the first counterbalance valve (14) in parallel, and the first pressure gauge (15) is installed at the first counterbalance valve (14). The second counterbalance valve 2 is installed at the second opening and used for adjusting the back pressure of the continuous slurry-bed tank reactor. The pressure of the second counterbalance valve (2) is set to a value higher than the sum of vapor pressures of system mediums by 0.2-1.0 MPa. The pressure of the second counterbalance valve (2) is set to the value lower than the designed pressure of the continuous slurry-bed tank reactor to avoid overpressure of the system when the system is abnormal and/or the reactants return before the feed pump. The second pressure gauge (1) is installed in a pipeline joining the second counterbalance valve (2) and the upper port of the four-way valve (3). The second pressure gauge (1) displays the back pressure of the continuous slurry-bed tank reactor, the third pressure gauge (12) shows its internal pressure, and the first pressure gauge (15) displays its front pressure.

The four-way valve (3) is used for switching the A tubular separation membrane (9) or the B tubular separation membrane (6) that are corresponding to the reaction mixture inlet and outlet so as to alternatively direct the reaction mixture flow into or out of the A tubular separation membrane (9) and the B tubular separation membrane (6), and thereby, to clean the catalyst adhered to the tubular separation membranes by the reverse reaction mixture flow and ensure that the A tubular separation membrane (9) and the B tubular separation membrane (6) are unblocked during the whole catalytic life of a catalyst.

The four-way valve (3) generally runs in a timing switching mode. Nonetheless, when the internal pressure of the tank reactor body is increased to 0.8 MPa, the four-way valve (3) also switches the flow direction.

When the continuous slurry-bed tank reactor runs, the liquid level is maintained between a reasonable upper limit and a lower limit, and the top portion of the tank reactor body (8) is filled with nitrogen gas. In the normal running process, reactants are fed into the continuous slurry-bed tank reactor at the preset flow rate. When the liquid level is relatively high, the filled nitrogen gas flow is speeded up for increasing the internal pressure of the continuous slurry-bed tank reactor. On the contrary, if the liquid level is relatively low, the filled nitrogen gas flow rate is lowered down.

When the liquid level of the continuous slurry-bed tank reactor is beyond the preset upper limit, the four-way valve (3) switches the flow paths.

When the flow path switching time interval of the four-way valve (3) is shorter than or equal to 2 hours, the liquid feed pump (13) stops operating, and the filling of the nitrogen gas is simultaneously stopped. After the permeability of the tubular separation membranes is confirmed to be declined, the continuous slurry-bed tank reactor is turned off, and the tubular separation membranes are replaced.

The liquid level of the reaction mixture in the tank reactor body is kept in an appropriate range by adapting the pressure of the nitrogen gas inside the tank reactor body to the feeding and discharging rates of the reaction mixture.

Figure 2:
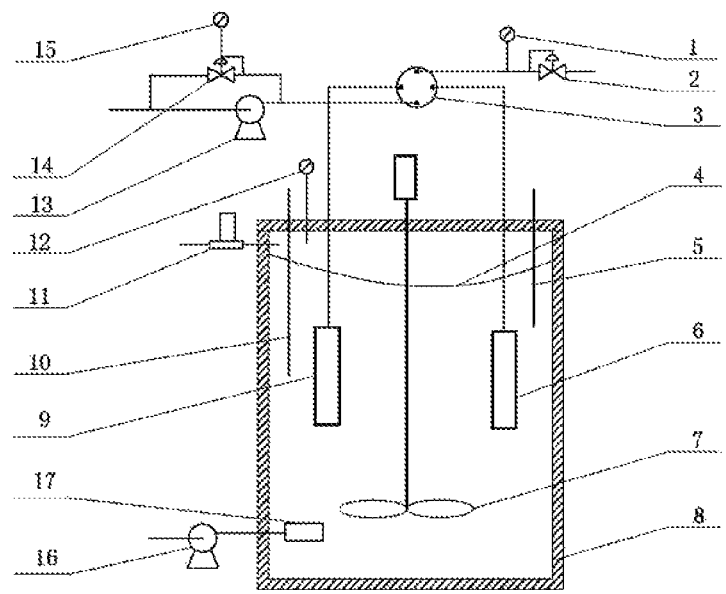
FIG. 2 is a schematic diagram of a continuous slurry-bed tank reactor with a function of feeding auxiliary materials.

Further, as is shown in FIG. 2, at least two auxiliary material spargers (17) are installed at the low portion of the side wall of the tank reactor body (8), and each one extends into the tank reactor body (8), is set up at a different position in the tank reactor body (8), and communicated with one auxiliary material feed pump (16) through another pipeline.

A method of using the continuous slurry-bed tank reactor comprises the following steps:

S1: adding a catalyst into the tank reactor body (8), and filling nitrogen gas in the tank reactor body (8) by the gas flow controller (11) until all air in the tank reactor body (8) is replaced with the nitrogen gas, wherein the gas flow controller (11) measures and controls the flow rate of the nitrogen gas filled in the tank reactor body (8);

S2: feeding reactants into the tank reactor body (8) sequentially through the liquid feed pump (13), the four-way valve (3) and the A tubular separation membrane (9); using a liquid level gauge to measure the liquid level of the fed reaction mixture and ensure that a distance between the liquid level of the reaction mixture and the top cap of the tank reactor body (8) is in the range of 5-80 cm; presetting the opening pressure of the first counterbalance valve (14) to a value lower than the designed pressure of the tank reactor body (8) by 0.3-0.5 MPa;

S3: when the liquid level of the reaction mixture is equal to the preset lower limit, stopping feeding the reactants; opening the heating system in the tank reactor body (8) to raise the internal temperature of the tank reactor body (8) to the designed temperature; opening the agitation system (7); determining the internal pressure of the tank reactor body (8) at this moment to be the initial pressure, and setting the opening pressure of the second counterbalance valve (2) to a value higher than the initial pressure by 0.3-0.8 MPa; maintaining the temperature for 1-3 hours after the internal temperature of the tank reactor body (8) is increased to the preset temperature; turning on the liquid feed pump (13) again to start continuously feeding the reactants;

S4: setting the four-way valve (3) to switch flow paths once every 4-8 hours for changing the direction of the reaction mixture flowing through the tubular separation membranes, wherein the four-way valve (3) switches the flow paths, and the switching time is concurrently reset when the internal pressure of the tank reactor body (8) is 0.8-1.0 MPa higher than the initially designed pressure; stopping feeding the reaction mixture when the flow path switching time interval is shorter than 2 hours due to an increase of the internal pressure of the tank reactor body (8).

Further, in step S2, at least two auxiliary material spargers (17) are installed at the lower portion of the side wall of the tank reactor body (8). The auxiliary material feed pump (16) adds reactants with poor miscibility in the tank reactor body (8) through the auxiliary material spargers (17).

Further, in step S3, when the liquid feed pump (13) starts continuously feeding the reactants, the gas flow controller (11) is turned on. First, a small flow of nitrogen gas is filled. Then, the flow rate of the nitrogen gas is dynamically adjusted in terms of the changes of the liquid level.

When the liquid level of the reaction mixture is close to the liquid level upper limit, the flow rate of the nitrogen gas is enlarged. On the contrary, if the liquid level of the reactants is approaching to the liquid level lower limit, the flow rate of the nitrogen gas is decreased. Notably, when the liquid level of the reaction mixture exceeds the liquid level upper limit, the four-way valve (3) is triggered to switch the flow paths. If the flow path switching time interval of the four-way valve (3) is shorter than 2 hours due to the increase of the internal pressure of the tank reactor body, the filling of nitrogen gas by the gas flow controller (11) would be stopped.

Further, the feeding amount of the liquid feed pump (13) is determined to be 0.3-50 $h^{-1}$ of the weight hourly space velocity on the basis of the reactant conversion and the product selectivity. When the flow path switching time interval of the four-way valve (3) is shortened due to the increase of the internal pressure or the change of the liquid level, the feeding amount of the reaction mixture is reduced until the catalytic performance of the catalyst or the permeability of the tubular separation membranes cannot meet the demands.

The following describes the current invention in detail by means of one or more embodiments:

Embodiment 1

2 kg MCM-22 molecular sieve catalyst with a Si/Al molar ratio of 100 is added in a 50 L tank reactor. Nitrogen gas is filled to replace air in the tank reactor. Liquid reactants of dimethoxymethane and 1,3,5-trioxane with a molar ratio of 2:1 are pumped into the tank reactor by a liquid feed pump (13) up to the distance between the liquid level and the top cap of the tank reactor body (8) of 15 cm. Then, the heating system of the tank reactor is started to raise the temperature inside the tank reactor body (8) to 50° C. Simultaneously, the agitation system (7) is initiated. After 2 hours, the liquid feed pump (13) restarts to continuously feed the reaction mixture. The opening pressure of counterbalance valve (2) is set to 0.5 MPa; the flow rate of the liquid feed pump (13) is set to 30 L/h; the flow path switching time interval of the four-way valve (3) is set to 6 hours; the starting pressure of counterbalance valve (14) is set to 1.2 MPa, and the initial flow rate of the gas flow controller (11) is set to 5 sccm that is later altered according to the changes of the liquid level in the following way. The flow rate of the gas flow controller (11) is increased with the elevation of the liquid level, but is decreased with the reduction of the liquid level. To maintain normal operation, the liquid level needs to intermediate between the upper limit of 5 cm and the lower limit of 15 cm far from the top cap of the tank reactor body (8).

The tank reactor continuously and stably runs. In the later process, the conversion of the reactants lowers down due to the deactivation of the catalyst. Thereafter, the reaction is stopped.

Embodiment 2

2 kg MCM-22 molecular sieve catalyst with a Si/Al molar ratio of 200 is added in a 50 L tank reactor. Nitrogen gas is filled to replace air in the tank reactor. Dimethoxymethane and 1,3,5-trioxane liquid mixture with a molar ratio of 2.5:1 are pumped into the tank reactor by the liquid feed pump (13) up to the distance between the liquid level and the top cap of the tank reactor body (8) of 15 cm. After that, the heating system of the tank reactor is opened to elevate the temperature of the tank reactor to 65° C. Simultaneously, the agitation system (7) is started. After 1 hour, the liquid feed pump (13) restarts to continuously feed the reactants. The opening pressure of counterbalance valve (2) is set to 0.8 MPa; the flow rate of the liquid feed pump (13) is set to 50 L/h; the flow path switching time interval of the four-way valve (3) is set to 4 hours; the opening pressure of counterbalance valve (14) is set to 1.2 MPa, and the initial flow rate of the gas flow controller (11) is set to 5 sccm that is adjusted in terms of the liquid level in the reaction process in the following way. The flow rate of the gas flow controller (11) is increased with the elevation of the liquid level, and is decreased with the decline of the liquid level. To maintain normal operation, the upper and the lower limits of the liquid level are set to 5 and 15 cm far from the top cap of the tank reactor body (8) respectively.

The tank reactor continuously and stably runs for more than 500 hours. In the later process, the conversion of the raw materials lowers down, but the selectivity to product is still high.

Embodiment 3

2 kg MCM-22 molecular sieve catalyst with a Si/Al molar ratio of 50 is added in a 50 L tank reactor. Nitrogen gas is filled to replace air in the tank reactor. Dimethoxymethane and 1,3,5-trioxane liquid mixture with a molar ratio of 2.5:1 are pumped into the tank reactor by a liquid feed pump (13) until the distance between the liquid level and the top cap of the tank reactor body (8) reaches 15 cm. Then, the heating system of the tank reactor is started to raise the temperature of the tank reactor to 35° C. Simultaneously, the agitation system (7) is initiated. After 3 hours, the liquid feed pump 13 restarts to continuously feed the reactants. The opening pressure of the counterbalance valve (2) is set to 0.3 MPa; the flow rate of the liquid feed pump (13) is set to 50 L/h; the flow path switching time interval of the four-way valve (3) is set to 8 hours; the opening pressure of the counterbalance valve (14) is set to 1.2 MPa, the initial flow rate of the gas flow controller (11) is set to 5 sccm that is adjusted according to the changes of the liquid level in the reaction process in the following way. The flow rate of the gas flow controller (11) is increased with the elevation of the liquid level, and is decreased with the decline of the liquid level. To maintain normal operation, the upper and the lower limits of the liquid level are set to 5 and 15 cm far from the top cap of the tank reactor body (8) respectively.

After the tank reactor continuously runs for more than 100 hours, the conversion of the reactants is slightly decreased although the selectivity to products is still high.

Embodiment 4

2 kg MCM-22 molecular sieve catalyst with a Si/Al molar ratio of 50 is added in a 50 L tank reactor. Nitrogen gas is filled to replace air in the tank reactor. Liquid reactants of dimethoxymethane and 1,3,5-trioxane with a molar ratio of 2.5:1 are pumped into the tank reactor by a liquid feed pump (13) until the distance between the liquid level and the top cap of the tank reactor body (8) reaches 15 cm. Afterwards, the heating system of the tank reactor is started to raise the temperature of the tank reactor to 35° C. Simultaneously, the agitation system (7) is initiated. After 3 hours, the liquid feed pump (13) restarts to continuously feed the reactants. The opening pressure of counterbalance valve (2) is set to 0.3 MPa; the flow rate of the liquid feed pump (13) is set to 50 L/h; the flow path switching time interval of the four-way valve (3) is set to 8 hours; the opening pressure of counterbalance valve (14) is set to 1.2 MPa, and the initial flow rate of a gas flow controller (11) is set to 5 sccm that is adjusted according to the changes of the liquid level in the reaction process in the following way. The flow rate of the gas flow controller (11) is enlarged with the elevation of the liquid level, and is decreased with the reduction of the liquid level. To maintain normal operation, the upper limit and the lower limit of the liquid level intermediates 5 and 15 cm far from the top cap of the tank reactor body (8).

The tank reactor continuously and stably runs. In the later process, the conversion of the reactants is slightly decreased due to the deactivation of the catalyst, thus the reaction is stopped.

Embodiment 5

3 kg Titanium silicalite molecular sieve catalyst is added to a 50 L tank reactor. Nitrogen gas is filled to replace air in the tank reactor. Benzene is pumped into the tank reactor by the liquid feed pump (13) until the distance between the liquid level and the top cap of the tank reactor body (8) reaches 15 cm. Afterwards, the heating system of the tank reactor is opened to raise the temperature of the tank reactor to 85° C. Simultaneously, the agitation system (7) is started. After 3 hours, the liquid feed pump (13) restarts to continuously feed the reactants. Hydrogen peroxide is pumped through the auxiliary material feed pump (16), and fed into the tank reactor by four auxiliary material spargers (17) at a rate of 5 L/h in different positions. The auxiliary material feed pump (16) and the liquid feed pump (13) are controlled to simultaneously start and stop. The opening pressure of the counterbalance valve (2) is set to 0.6 MPa; the flow rate of the liquid feed pump (13) is set to 20 L/h; the flow path switching time interval of the four-way valve (3) is set to 4 hours; the opening pressure of the counterbalance valve (14) is set to 1.8 MPa, the initial flow rate of the gas flow controller (11) is set to 5 sccm that is adjusted in terms of the changes of the liquid level in the reaction process in the following way. The flow rate of the gas flow controller (11) is increased with the elevation of the liquid level, and is decreased with the decline of the liquid level. To maintain normal operation, the upper and the lower limits of the liquid level are set to 10 and 20 cm far from the top cap of the tank reactor body (8) respectively. When the distance between the liquid level and the top cap of the tank reactor body (8) is shorter than 10 cm, the auxiliary material feed pump (16) and the auxiliary material spargers (13) are stopped.

Embodiment 6

3 kg Titanium silicalite molecular sieve catalyst is added in a 50 L tank reactor. Nitrogen gas is filled to replace air in the tank reactor. Cyclohexanone is pumped into the tank reactor by a liquid feed pump (13) up to the distance between the liquid level and the top cap of the tank reactor body (8) of 15 cm. Afterwards, the heating system of the tank reactor is started to raise the temperature of the tank reactor to 75° C. Simultaneously, the agitation system (7) is initiated. After 2 hours, the liquid feed pump (13) restarts to continuously feed the reactants. Hydrogen peroxide is pumped through the auxiliary material feed pump (16), and fed into the tank reactor by four auxiliary material spargers (17) at a rate of 10 L/h in different positions. The auxiliary material feed pump (16) and the liquid feed pump (13) are controlled to simultaneously start and stop. The opening pressure of the counterbalance valve (2) is set to 0.6 MPa; the flow rate of the liquid feed pump (13) is set to 30 L/h; the flow path switching time interval of the four-way valve (3) is set to 4 hours; the opening pressure of the counterbalance valve (14) is set to 1.6 MPa, and the initial flow rate of the gas flow controller (11) is set to 5 sccm that is adjusted according to the changes of the liquid level in the following way. The flow rate of the gas flow controller (11) is increased with the elevation of the liquid level, and is decreased with the reduction of the liquid level. To maintain normal operation, the upper and the lower limits of the liquid level is 8 and 20 cm far from the top of the tank reactor body (8) respectively. When the distance between the liquid level and the top cap of the tank reactor body (8) is less than 8 cm, the auxiliary material feed pump (16) and the auxiliary material spargers (13) are stopped.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A continuous slurry-bed tank reactor, comprising a tank reactor body, an agitator and tubular separation membranes, wherein the tank reactor body comprises a bottom, a side wall, an upper/top cap, and configured for holding a heterogeneous and nanomaterial-based catalyst and equipped with a thermocouple for measuring an internal temperature of the tank reactor body, a liquid level gauge for measuring a liquid level inside the tank reactor body, a third pressure gauge for measuring an internal pressure of the tank reactor body, and a gas flow controller for measuring a gas flow rate into the tank reactor body;

the agitator comprises an agitation motor, an agitation shaft and an agitation impeller; the agitation motor is set up at a center over the tank reactor body; a rotor of the agitation motor is vertically downwards installed; one end of the agitation shaft is fixedly connected with the rotor of the agitation motor, and a bottom end thereof penetrates through the upper/top cap of the tank reactor body and extends to the bottom of the tank reactor body; the agitation impeller is located at the bottom end of the agitation shaft;

the tubular separation membranes comprise an A tubular separation membrane and a B tubular separation membrane, which are respectively vertically downwards positioned on two sides of the agitation shaft in the tank reactor body; the A tubular separation membrane and the B tubular separation membrane both utilize stainless steel tubes fabricated in a powder metallurgy manner as a substrate, and permeabilities of the A tubular separation membrane and the B tubular separation membrane are finely adjusted through chemical vapor deposition, such that solid catalysts with different particle sizes is separated from liquid reactants; a first opening and a second opening of the continuous slurry-bed tank reactor are respectively communicated with two transversely symmetrical ports of a four-way valve outside the tank reactor body; the A tubular separation membrane and the B tubular separation membrane are respectively communicated with two longitudinally symmetrical ports of the four-way valve; the first opening and the second opening do not simultaneously feed or discharge liquid; a liquid feed pump is set up outside the tank reactor body at the first opening and connected with a first counterbalance valve in parallel, a first pressure gauge is installed at the first counterbalance valve outside the tank reactor body; an opening pressure of the first counterbalance valve is set to a value lower than a predetermined pressure of the tank reactor body by 0.3-0.5 MPa; a second counterbalance valve is located outside the tank reactor body near the second opening, and a second pressure gauge is installed in a first pipeline communicated with the second counterbalance valve and an upper port of the four-way valve; and a pressure of the second counterbalance valve is set to a value lower than a predetermined pressure of the tank reactor body;

the liquid level measured by the liquid level gauge is maintained between a predetermined upper limit and a predetermined lower limit by adapting pressure of gas inside the tank reactor body to feeding rate and discharging rate of reaction mixture in the tank reactor body, and when the liquid level measured by the liquid level gauge is beyond the predetermined upper limit, the four-way valve is configured to switch flow paths.

2. The continuous slurry-bed tank reactor according to claim 1, wherein at least two auxiliary material spargers are installed at a lower portion of a side wall of the tank reactor body; and each one extends into the tank reactor body and is communicated with an auxiliary material feed pump through a second pipeline.

3. A method of using the continuous slurry-bed tank reactor according to claim 1, comprising the following steps:

S1: adding the catalyst in the tank reactor body, and filling nitrogen gas in the tank reactor body by the gas flow controller until all air in the tank reactor body is replaced with the nitrogen gas, wherein the gas flow controller measures and controls a flow rate of the nitrogen gas filled in the tank reactor body;

S2: feeding reactants into the tank reactor body sequentially through the liquid feed pump, the four-way valve and the A tubular separation membrane; using the liquid level gauge to measure a liquid level of fed reactants and ensure that a distance between the liquid level of the fed reactants and a top cap of the tank reactor body is in a range of 5-80 cm; presetting an opening pressure of the first counterbalance valve to a value lower than a designed pressure of the tank reactor body by 0.3-0.5 MPa;

S3: when the liquid level of the fed reactants reaches a preset lower limit, stopping feeding the reactants; starting a heating system in the tank reactor body to raise the internal temperature of the tank reactor body to a preset temperature, and simultaneously opening the agitator; determining the internal pressure of the tank reactor body at this moment as an initial pressure, and setting an opening pressure of the second counterbalance valve to a value higher than the initial pressure by 0.3-0.8 MPa; keeping the preset temperature for 1-3 hours after the internal temperature of the tank reactor body is raised to the preset temperature; turning on the liquid feed pump to continuously restart feeding the reactants;

S4: setting the four-way valve to switch flow paths once every 4-8 hours for changing directions of the reactants flowing through the tubular separation membranes, wherein the four-way valve also switches the flow paths, and a time interval for switching the flow paths switching time interval is reset when the internal pressure of the tank reactor body is 0.8-1.0 MPa higher than the initial pressure; stopping feeding the reactants when the time interval for switching the flow paths is shorter than 2 hours due to an increase of the internal pressure of the tank reactor body.

4. The method of using the continuous slurry-bed tank reactor according to claim 3, wherein in step S2, at least two auxiliary material spargers are installed at a lower portion of the side wall of the tank reactor body; the auxiliary material feed pump adds reactants with poor miscibility in the tank reactor body through at least the auxiliary material spargers.

5. The method of using the continuous slurry-bed tank reactor according to claim 3, wherein in step S3, when the liquid feed pump starts continuously feeding the reactants, the gas flow controller is turned on; first, a small flow of nitrogen gas is filled; then, the flow rate of the nitrogen gas is dynamically adjusted according to change(s) of the liquid level; when a liquid level of the reactants is close to a liquid level upper limit, the flow rate of the nitrogen gas is increased; on the contrary, while the liquid level of the reactants is approaching to the liquid level lower limit, the flow rate of the nitrogen gas is decreased; when the liquid level of the reactants is beyond the liquid level upper limit, the four-way valve is triggered to switch the flow paths; if the time interval for switching the flow paths of the four-way valve is shorter than 2 hours due to the increase of the internal pressure of the tank reactor body, filling of the nitrogen gas would be stopped by closing the gas flow controller.

6. The method of using the continuous slurry-bed tank reactor according to claim 3, wherein a feeding amount of the liquid feed pump is determined to be 0.3-50 $h^{-1}$ of a weight hourly space velocity in terms of a reactant conversion and a product selectivity; when the time interval for switching the flow paths of the four-way valve is decreased due to an enhancement of the internal pressure or a change of the liquid level, the feeding amount of the reactants is reduced until catalytic performance of the catalyst and/or a permeability of the tubular separation membranes cannot meet demands.

* * * * *